US006754306B2

(12) United States Patent
Cho et al.

(10) Patent No.: US 6,754,306 B2
(45) Date of Patent: Jun. 22, 2004

(54) PORTABLE MEDICAL DIGITAL RADIOGRAPHY ASSEMBLY

(75) Inventors: Kenneth Cho, Honolulu, HI (US); Mark Freckleton, San Antonio, TX (US); Peter Martin, Kihei Maui, HI (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 10/300,935

(22) Filed: Nov. 21, 2002

(65) Prior Publication Data

US 2003/0142788 A1 Jul. 31, 2003

Related U.S. Application Data

(60) Provisional application No. 60/331,761, filed on Nov. 21, 2001.

(51) Int. Cl.[7] .................................................. H05G 1/24
(52) U.S. Cl. ....................................... 378/102; 378/189
(58) Field of Search ................................ 378/102, 189, 378/195, 197, 193, 98.8, 206, 208, 19, 42, 45, 55, 62, 196

(56) References Cited

U.S. PATENT DOCUMENTS

| | | | | |
|---|---|---|---|---|
| 601,172 A | * | 3/1898 | Seguy | |
| 4,813,060 A | * | 3/1989 | Heubeck et al. | ............... 378/39 |
| 4,984,774 A | * | 1/1991 | Zupancic et al. | ............... 5/601 |
| 5,086,447 A | * | 2/1992 | Siczek et al. | ................ 378/197 |
| 5,521,957 A | * | 5/1996 | Hansen | ........................ 378/198 |
| 5,909,478 A | | 6/1999 | Polichar et al. | |
| 6,206,566 B1 | * | 3/2001 | Schuetz | ........................ 378/205 |
| 6,256,374 B1 | * | 7/2001 | Tomasetti et al. | ........... 378/98.2 |
| 6,315,445 B1 | | 11/2001 | Mazess et al. | |
| 6,379,041 B1 | | 4/2002 | Schuetz et al. | |
| 6,398,409 B1 | | 6/2002 | Brooks | |

OTHER PUBLICATIONS

Trex Enterprises, "PDX 2000: Portable Digital X–Ray System," printed from www.trexenterprise.com dated Jul. 6, 2003, pp. 1–2.

* cited by examiner

*Primary Examiner*—Craig E Church
*Assistant Examiner*—Irakli Kiknadze
(74) *Attorney, Agent, or Firm*—Elizabeth Arwine

(57) ABSTRACT

A portable medical digital radiography apparatus includes a ruggedized transport case housing several system components, a digital X-ray image sensor and an X-ray generator. The digital X-ray image sensor is hingedly coupled to a stand that is mounted to the ruggedized transport case. The X-ray generator is preferably positioned opposite to the center of digital X-ray image sensor. A patient support unit is disposed between digital X-ray image sensor and the X-ray generator. An image acquisition unit is connected to the X-ray generator and to the digital X-ray image sensor and fixedly mounted in the ruggedized transport case. An image display unit is connected to the image acquisition unit and spaced from the X-ray generator.

10 Claims, 4 Drawing Sheets

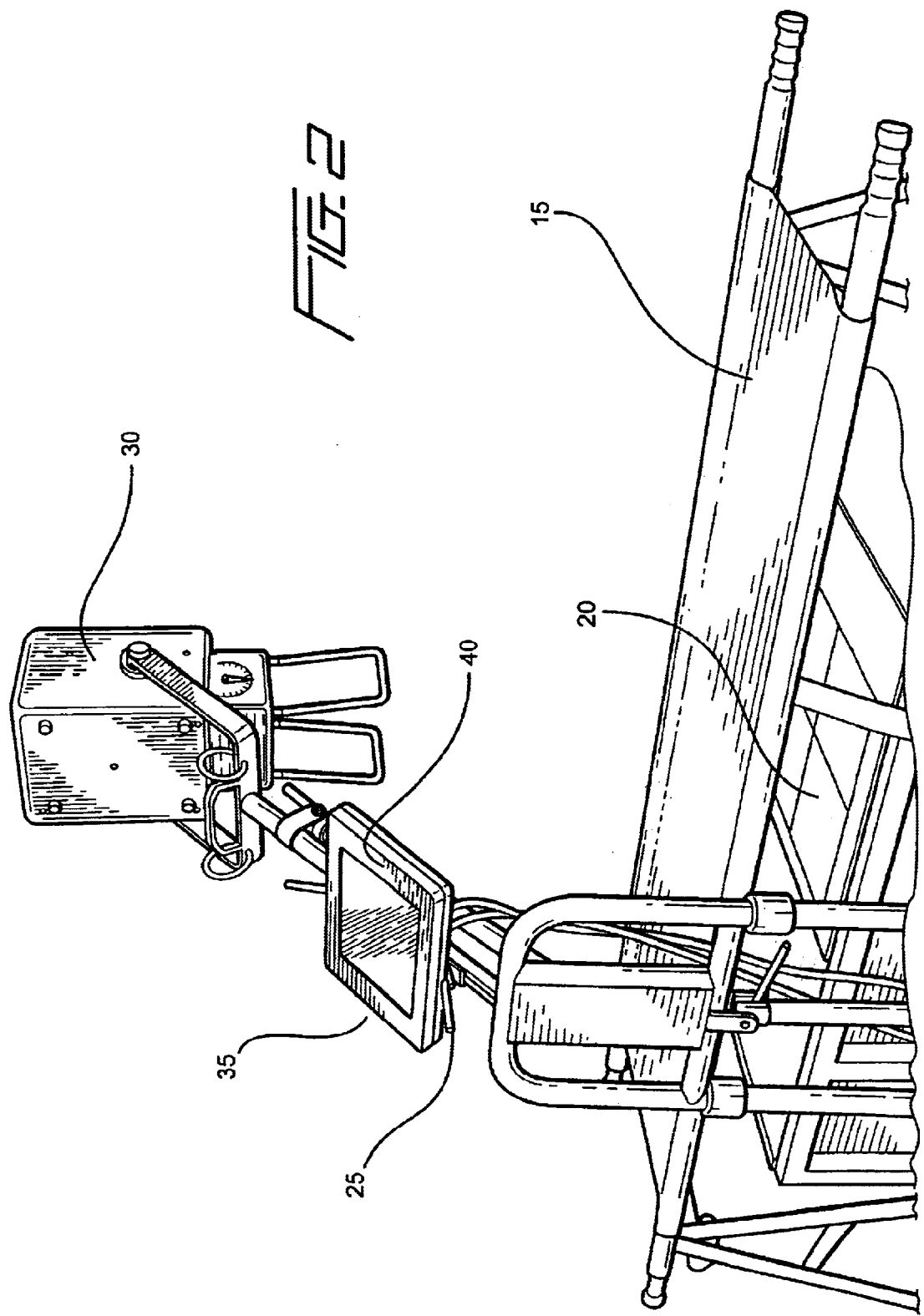

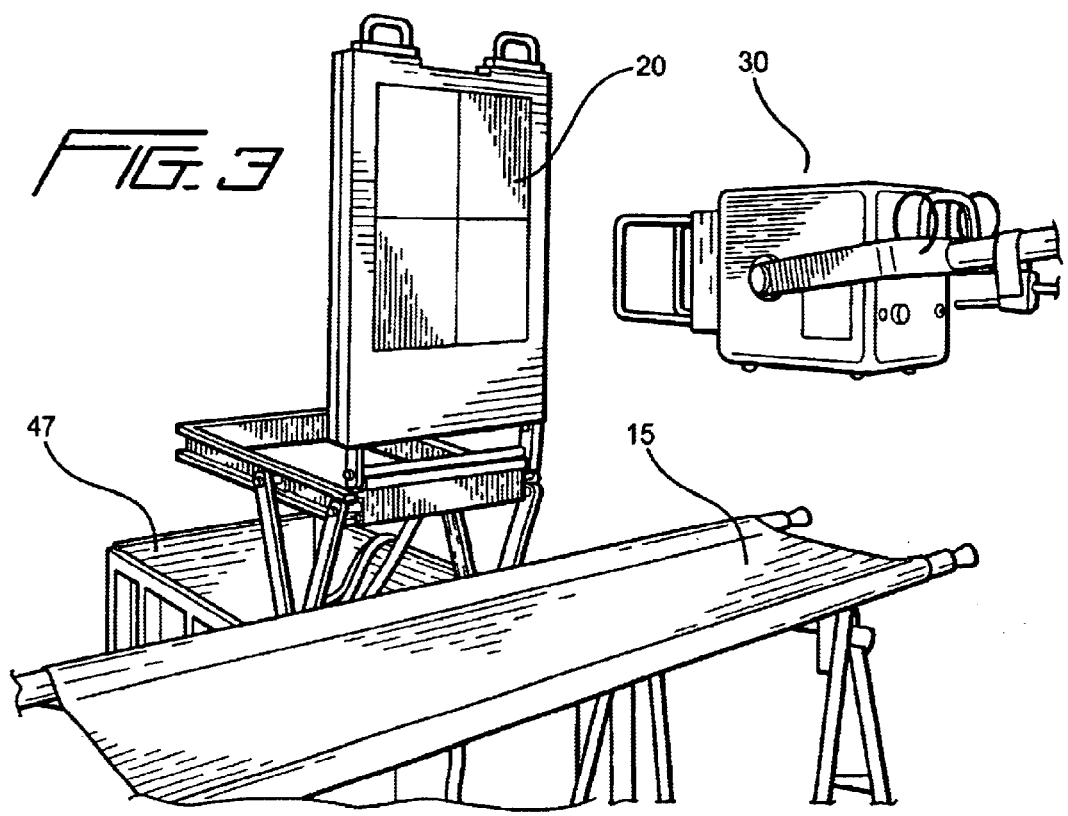
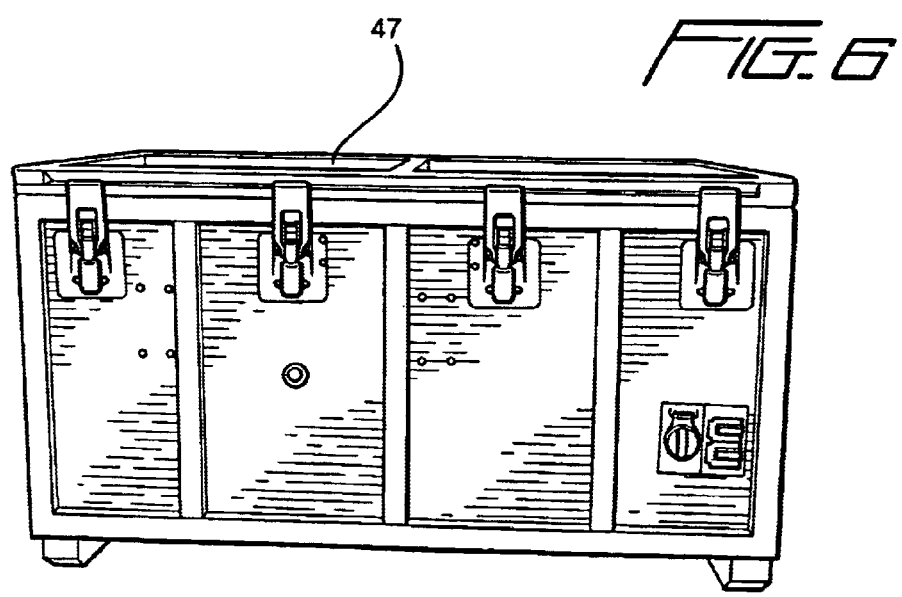

PORTABLE MEDICAL DIGITAL RADIOGRAPHY ASSEMBLY

I. FIELD OF THE INVENTION

This invention relates to the field of radiology and, more specifically to the field of mobile field radiology.

II. BACKGROUND OF THE INVENTION

There are numerous situations in the medical field where it is desirable to obtain a radiographic image of a living being located in the field who is suspected of being injured without transporting the living being to a hospital or clinical setting. For example, military medical personnel are constantly treating injured soldiers on the battlefield. Frequently, the injured soldiers should not or cannot be transported to a hospital or clinical setting. Similarly, athletes are frequently injured on the field or court and require immediate attention. Because injured athletes are sometimes rendered unconscious or incoherent, athletic medical personnel cannot always detect the extent of the athlete's injury by communicating with the athlete.

Heretofore, it has been necessary to transport injured persons to hospitals or other clinical facilities before X-rays could be taken. If the extent of the person's injuries are unknown, the act and manner of transporting the person can often exacerbate the injury. Accordingly, to minimize the chances of aggravating injuries due to transport, there is a need for a device that produces X-rays in field at the injury site.

III. SUMMARY OF THE INVENTION

An objective of the invention is to provide a device and method for facilitating rapid, on the spot diagnosis of injuries in the field.

It is another objective of the invention is to provide a digital X-ray unit that is effective for field use.

It is still a further object of the invention to provide a device that performs direct digital capture of medical radiographic images in the field and permits soft copy viewing of those images.

Given the following enabling description of the drawings, the apparatus should become evident to a person of ordinary skill in the art.

IV. BRIEF DESCRIPTION OF THE DRAWINGS

Like reference numerals in the figures represent and refer to the same element or function throughout.

FIG. 2 is an illustration of an imaging system depicting an X-ray image sensor in a horizontal position, according to an embodiment of the present invention.

FIG. 3 is an illustration of an imaging system depicting an X-ray image sensor in a vertical position, according to an embodiment of the present invention.

FIG. 6 is an illustration of a transport box according to an embodiment of the present invention.

V. DETAILED DESCRIPTION OF THE DRAWINGS

Figure 1:
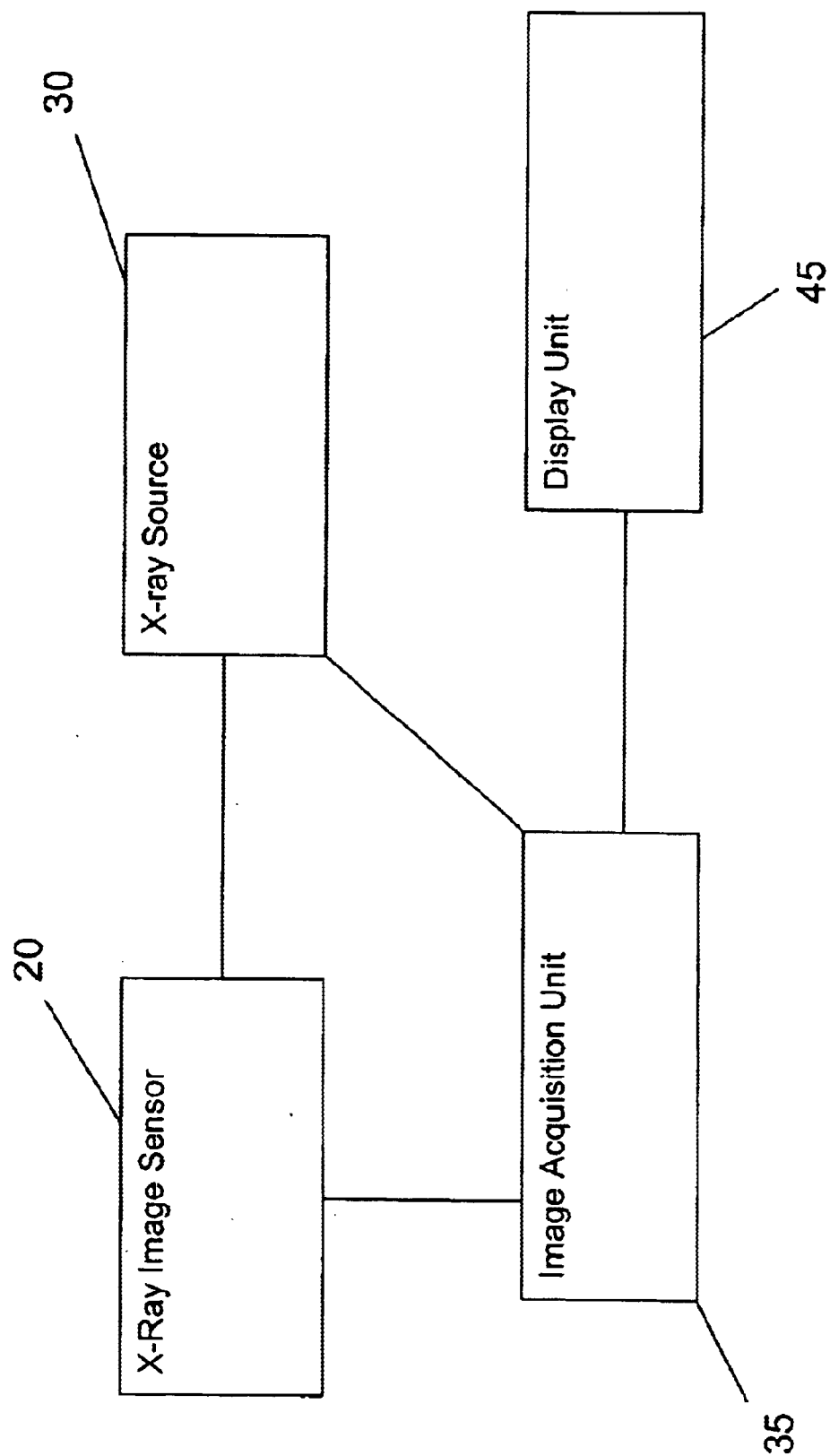
FIG. 1 is a block diagram of an imaging system according to an embodiment of the present invention.

The present invention is directed to a portable digital radiography device that is particularly suited to radiography outside of the hospital or controlled setting, e.g., mobile field radiography. The device is self-contained and may be stored in a mobile, rugged transport box. Referring now to the drawings, FIG. 1 depicts an imaging system 10 according to the invention, primarily intended for generating X-rays of the human body. The imaging system 10, includes a patient support unit 15, a digital X-ray image sensor 20, an adjustable height stand 25 supporting the digital X-ray image sensor 20, an X-ray source 30, a image acquisition unit 35 and an image acquisition and display unit 45. In accordance with an aspect of the invention, the foregoing components may be arranged and stored within a ruggedized transport box 47 to facilitate transport to the location of the injured patient. In accordance with another aspect of the invention, the components may be assembled and interconnected in a specific arrangement to facilitate imaging of the human body.

In accordance with an embodiment of the invention, the components comprising imaging system 10 are preferably arranged and interconnected as described herein. More particularly, as shown in FIG. 2, in one embodiment, digital X-ray image sensor 20 is attached to height adjustable stand 25 which, in turn, is attached to transport box 47 such that digital X-ray image sensor 20 faces upward. Patient support unit 15 is disposed above digital X-ray image sensor 25. X-ray source 30 is preferably positioned directly above digital X-ray image senor 25 to facilitate image generation. In order to synchronize the operation of digital X-ray image sensor 25 and X-ray source 30, image acquisition unit 35 is coupled to both digital X-ray image sensor 20 and X-ray source 30. Image acquisition unit 35 preferably includes a display 40 to allow the user to view information relating to the control and operation of the digital X-ray senor 20 and the X-ray source 30. In particularly preferred embodiments, display 40 comprises a touchscreen display.

An image display unit may also be provided to permit the radiologist to view the images at a distance from X-ray generator 30 thus minimizing the radiologist's exposure to radiation. Image acquisition and display unit 45 may be connected to image acquisition unit 35 and preferably disposed at least 2 to 3 feet away from X-ray generator 30. Alternatively, image display unit 45 and image acquisition unit 35 may comprise a single machine.

Turning to the specific embodiments. In keeping with the invention, patient support unit 15 is provided for supporting the patient during the X-ray procedure. Patient support unit 15 may comprise any structure that will support the patient and will permit X-rays to pass therethrough with sufficient strength to be detected by digital X-ray image sensor 20. In a preferred embodiment, patient support unit 15 comprises a flexible stretcher that is transparent to 70–100 kVp X-rays that are preferable for use in field radiographic imaging. A suitable stretcher is the RAVEN™ manufactured by Reeves Manufacturing, Inc. of Frederick, Md. Patient support unit 15 also includes a pair of liter stands that stabilize the patient support unit 15 a desired distance above ground level.

In accordance with the invention, digital X-ray image sensor 20 is preferably a thin-film transistor (TFT) based digital X-ray image sensor. Preferably, digital image sensor 20 is about the same size as standard medical x-ray film (17"×17" image format). Digital X-ray image sensor products are commercially available from several companies including Canon, Varian, Trixxel, General Electric, and iiRad. These sensors can be grouped into two categories 1) indirect x-ray sensors (Canon, Varian, Trixxel) and 2) direct x-ray sensors (iiRad). The indirect x-ray sensors feature a TFT photodiode array that is sensitive to optical radiation (i.e. visible light). These sensors are covered by an x-ray to light converter such as gadolinium oxisulfide (Kodak Lanex®) or cesium iodide which converts each incident x-ray photon into a shower of optical photons. The optical photons are converted into electronic charge at each pixel photodiode. The direct x-ray sensor is coated with amorphous selenium which converts incident x-rays directly into electronic charge at each pixel. In both cases, the electronic charge distribution collected by the pixel array is proportional to the intensity distribution of x-ray photons; this charge distribution (i.e. x-ray image) is digitized and stored in a computer.

For field use, indirect detection type sensors are preferred. Indirect detection sensors covered with Lanex® screens are particularly preferred. In a preferred embodiment, digital X-ray image sensor 20 is a Canon CXDI-22 sensor including a 17"×17" image array of 2688×2688 pixels (160 micron pixels) is particularly preferred because it is large enough to match the size of a standard chest X-ray (17"×14"). Digital X-ray image sensor 20 preferably generates a 14-bit digital image that may be captured by image acquisition unit 35. The Canon CXDI-22 sensor has the specifications set forth in Table 1.

TABLE 1

| PARAMETER | SPECIFICATION |
| --- | --- |
| Image Sensor Panel | |
| Sensor Type | Amorphous Silicon Thin-Film Transistor (TFT) Array |
| Image Format | 17" × 17" (43 cm × 43 cm) |
| Pixel Count | 2,688 × 2,688 pixels (7.2 million pixels) |
| Pixel Pitch | 160 microns |
| X-ray-to-light converter | Lanex Regular |
| Resolution | 3.1 lp/mm |
| Gray Scale Resolution | 12-bit (4096) |
| Dynamic Range | 10,000 |
| Refresh Cycle | 6 seconds |
| Anti-Scatter Grid | 10:1, 40 lp/cm |
| Power Supply | Low-noise analog supply |
| Operating Temperature | 50–95 degrees centigrade |
| Operating Humidity | 30–75% RH |
| Dimensions | 21.6" × 25.4" × 2.9" |
| Weight | 77 lbs. |
| Source to Image Distance Focal Length | 110 cm |
| Control PC Unit | |
| Processor | Dual Pentium III 500 MHz |
| Storage | 13 GB Hard Drive (750 images) |
| Interface | Ethernet 10/100 Base T |

Figure 4:
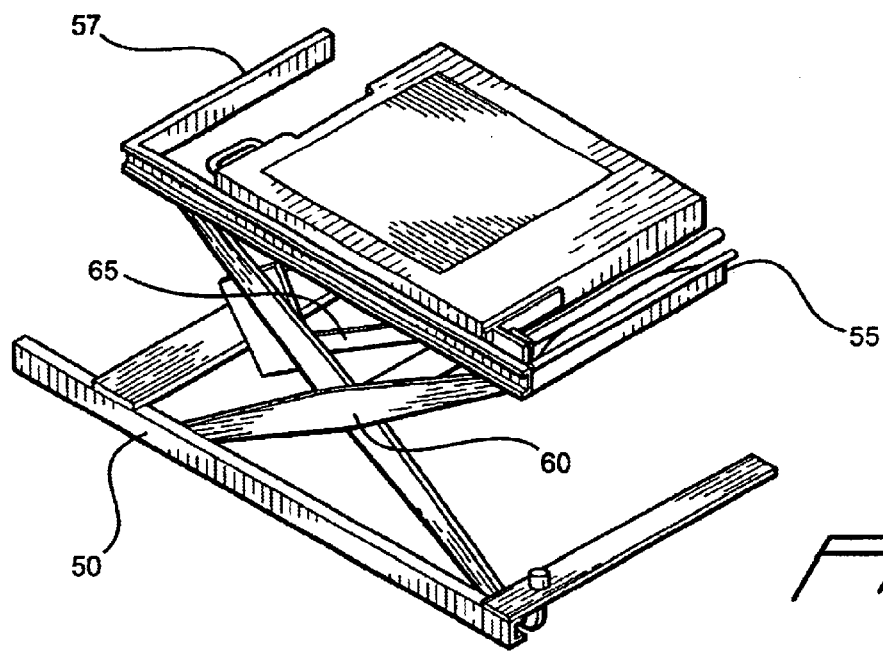
FIG. 4 is an illustration of an adjustable height stand according to an embodiment of the present invention.

As mentioned above, adjustable height stand 25 is provided for supporting and positioning digital X-ray image sensor 20. As illustrated in FIG. 4, adjustable height stand 25 preferably includes a base 50, a hinge assembly 55 and a scissor structure 60 interconnecting base 50 and frame 57. Digital is X-ray image sensor 20 is preferably connected to hinge assembly 55 which is in turn connected to frame 57 as shown in FIG. 4. Adjustable height stand 25 also includes a pneumatic strut sub-assembly 65 that urges against digital X-ray image sensor 20. Accordingly, the radiologist can lift digital X-ray image sensor 20 from its horizontal rest position (FIG. 2) and position it vertically as illustrated in FIG. 3 to accommodate standing patients. In that case pneumatic strut sub-assembly 65 will hold digital X-ray image sensor 20 in the vertical position.

In particularly preferred embodiments, adjustable height stand 25 may be raised and lowered by a motor (not shown) that controls scissor structure 60. Alternatively, adjustable height stand 25 may be manually lowered and raised.

As illustrated in FIGS. 2 and 3, X-ray source 30 is preferably a mobile unit that is capable of being positioned at various orientations. X-ray source 30 preferably conforms to the specifications set forth in Table 2 below

TABLE 2

| Parameter | Specification |
| --- | --- |
| Tube Voltage | 40–100 kVDC |
| Exposure Range | .01–4 seconds |
| Tube Current | 20 mA |
| Weight | 85 lbs with stand |
| Tubehead Size | 24" × 12" × 9" |
| Input Power | 20 A @ 120 V |

Figure 5:
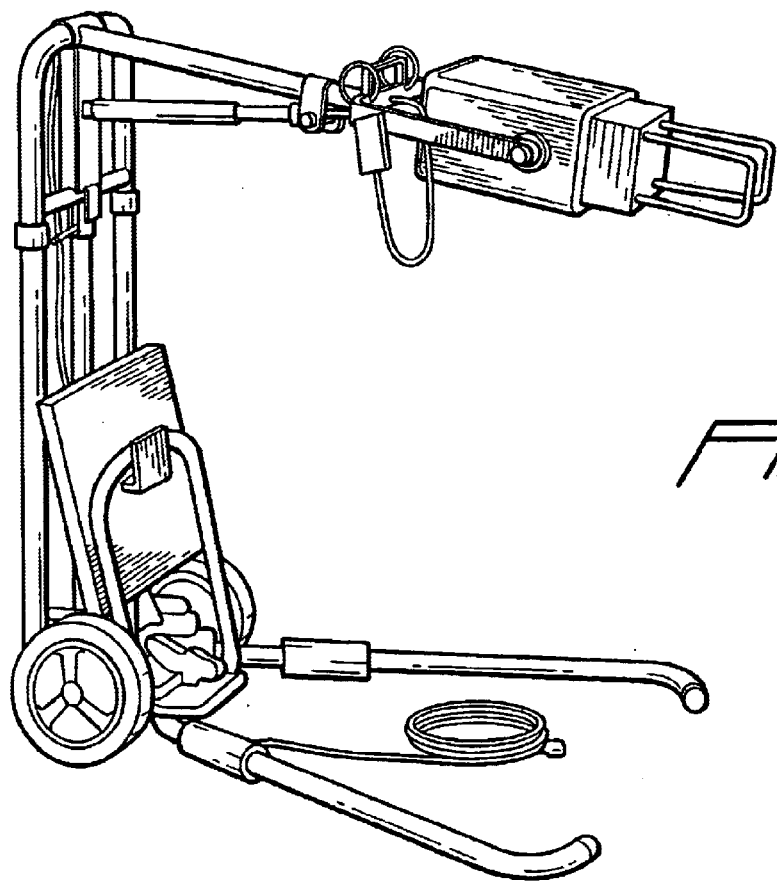
FIG. 5 is an illustration of an exemplary X-ray generator according to an embodiment of the present invention.

As shown more particularly in FIG. 5. an exemplary X-ray generator 30 includes a tubehead 70 articulatingly coupled to arm 75, which, in turn is articulatingly coupled to stand 80. In preferred embodiments, tubehead 70 includes an optical alignment subsystem that enables fine alignment with digital X-ray image sensor 20. In order to facilitate mobility, stand 80 is provided with wheels 85. Floor legs 90 are provided to balance X-ray generator 30.

To coordinate the operation of digital X-ray image sensor 20 and X-ray source 30, image acquisition unit 35 is provided. Image acquisition unit 35 may be a PC loaded with software for operating digital X-ray image sensor 20 and the X-ray source 30. A preferred PC is the Dell Dimension PC. Image acquisition unit 35 preferably includes a minimum 233 MHz processor, more preferably a 400 MHz or higher processor and at least 512 Mb of RAM, more preferably 1 GB or more of RAM. Image acquisition unit 35 preferably includes a number of peripherals including an Ethernet 10BaseT card, a 3.5" floppy drive, at least a 20 GB hard drive, and a read only or a read/write CD ROM drive. Image acquisition unit further includes a video controller, e.g., ATI Rage 128 Pro; at least 16 Mb and more preferably 32 Mb of video memory, a PCI bus interface with at least 5 PCI slots, and the WINDOWS NT or WINDOWS 2000 operating system. In addition, in order to be useful in a wide range of field conditions, image acquisition unit 35 preferably operates at temperatures between 0 deg. C. to 50 deg C., may be stored at temperatures between 0 deg C. to 70 deg C. and preferably operates at humidity levels from 0% to 95% non-condensing.

In particularly preferred embodiments, image acquisition unit 35 is connected to a touchscreen display 95. Touchscreen display 95 may be disposed or mounted onto any structure that would make access convenient for the radiologist, e.g., transport box 47, a table, a tent pole, or even the ground. A preferred touchscreen conforms to the specifications set forth below in Table 3. However, other touchscreen displays may be employed without departing from the spirit of the invention.

TABLE 3

| Parameter | Specification |
| --- | --- |
| Display Area | 36 cm × 46 cm |
| Drive System | a-Si TFT active matrix |
| Pixel Count | 1280 × 1024 |
| Size | 470 × 382 × 45 mm |
| Contrast Ratio | 100:1 |
| Luminance | 200 nit |

TABLE 3-continued

| Parameter | Specification |
| --- | --- |
| Supply Voltage | 120 V |
| Power Consumption | 65 W |
| Size | 45 cm × 36 cm × 11 cm |
| Relative Humidity | 10% to 85% |
| Weight | 18 lb |
| Operator Input | touchscreen option, capacitive touch |
| storage temperature | −20 C. to 60 C. |

In a preferred embodiment of the invention, imaging system 10 is provided with an image display unit 45. In some embodiments, image display unit 45 may comprise a computer, preferably a laptop computer, e.g. a Dell 8000 Laptop. Preferred specifications for image display unit 45 are set forth in Table 4 below.

TABLE 4

| Parameter | Specification |
| --- | --- |
| Processor | Pentium III, 800 MHz |
| Memory | 256 MB |
| Hard Drive | 20 GB |
| Operating System | Windows 2000 |
| Modem | MINIPCI 56K |
| CD-ROM Drive | 8X CDRW |

In order to display images generated by digital X-ray image sensor 30, image display unit 45 is provided with image viewing software that at least supports images in DICOM and JPEG format. Preferred software is Radworks 5.0 available from GE Medical Systems Information Technologies Applicare Center of Excellence of the Netherlands (www.applicare.com). An advantage of employing image display unit 45 to display images is that it can be spaced from X-ray source 30 thus allowing the radiologist to view images with a reduced risk of harmful exposure to radiation.

In an alternative embodiment, instead of providing a separate machine to perform the image display function, image display software may be loaded onto image acquisition unit 35 to allow that unit to perform the image display function.

In keeping with the invention, all of the components of imaging system 10 described above excepting X-ray generator 30 may be loaded into transport box 47. In accordance with a preferred aspect of the invention, several components are fixedly mounted to transport box 47. For example, image acquisition unit 35 is Image acquisition unit 35 is mounted inside transport box 47 as are system power supplies (not shown). Also, adjustable height stand 25 is preferably mounted to the bottom of transport box box 47. This ensures a level surface for stand 25 and facilitates raising and lowering of digital X-ray image sensor 20. As illustrated in FIG. 6, transport box 47 may be used to stabilize X-ray generator 30. Floor legs 90 may be positioned underneath the transport box 47. The transport box 47 is equipped with risers to facilitate forklift transport, and the system is designed so that floor legs 90 are positioned against the inside of one of the risers. This approximately aligns the tubehead 70 with the center of the digital x-ray image sensor 20.

We claim:

1. A portable digital medical radiography device comprising:

a patient support unit;

a digital X-ray image sensor detached from and positioned proximate to said patient support unit;

an adjustable height stand including a base, a frame, and a scissor structure interconnecting said base and said frame, said digital X-ray image sensor being connected to said frame;

an X-ray source for generating X-rays;

an image acquisition unit coupled to said digital X-ray sensor and said X-ray source for controlling the operation of said X-ray source and said X-ray sensor such that said digital X-ray image sensor generates images responsive to X-rays generated by said X-ray source and for retrieving the generated images.

2. The portable digital medical radiography device of claim 1 further comprising an image display unit for displaying one or more of (i) images retrieved by said image acquisition unit, ii) images stored in said image acquisition unit and iii) images generated by said digital X-ray image sensor.

3. The portable digital medical radiography device of claim 2 wherein said adjustable height stand includes a base, a hinge assembly and a scissor structure interconnecting the base and hinge assembly, said X-ray image sensor being attached to hinge assembly and being rotatable through an angle of at least 90°.

4. A portable digital medical radiography device comprising:

a ruggedized transport box;

a digital X-ray image sensor;

an adjustable height stand including a hinge assembly coupled to said digital X-ray image sensor and a base fixedly connected to an inner surface of said ruggedized transport box;

a patient support unit disposed proximate to said digital X-ray image sensor for supporting a patient thereon;

an X-ray source for generating X-rays, said X-ray source being substantially aligned with a center of said digital X-ray image sensor;

an image acquisition unit coupled to said digital X-ray sensor and said X-ray source for synchronizing said X-ray source to said X-ray sensor such that said digital X-ray image sensor generates images responsive to X-rays generated by said X-ray source, said image acquisition unit being fixedly mounted to said ruggedized transport box; and an image display unit coupled to said image acquisition unit for displaying the generated images.

5. A portable digital medical radiography device comprising:

a ruggedized transport box;

a digital X-ray image sensor;

an adjustable height stand including a base, a hinge assembly and a scissor structure interconnecting the base and hinge assembly, said X-ray image sensor being attached to said hinge assembly and being rotatable through an angle of at least 90°, a patient support unit disposed proximate to said digital X-ray image sensor for supporting a patient thereon;

an X-ray source for generating X-rays, said X-ray source being substantially aligned with a center of said digital X-ray image sensor; and an image acquisition unit coupled to said digital X-ray sensor and said X-ray source for synchronizing said X-ray source to said X-ray sensor such that said digital X-ray image sensor generates images responsive to X-rays generated by said X-ray source, said image acquisition unit being fixedly mounted to said ruggedized transport box.

6. The portable digital medical radiography device of claim 5, further including a stand coupled to said X-ray source.

7. The portable digital medical radiography device of claim 6 further including a tubehead coupled to said stand.

8. The portable digital medical radiography device of claim 7, wherein said tubehead includes an optical alignment subsystem for enabling alignment with said digital X-ray image sensor.

9. The portable digital medical radiography device of claim 5, wherein said image acquisition unit is a personal computer.

10. The portable digital medical radiography device of claim 5, wherein said digital X-ray image sensor is a transistor based digital X-ray image sensor.

* * * * *